(12) United States Patent
Fleming et al.

(10) Patent No.: US 6,545,165 B1
(45) Date of Patent: Apr. 8, 2003

(54) SYNTHESIS OF 3,6-DIALKYL-5,6-DIHYDRO-4-HYDROXY-PYRAN-2-ONE

(75) Inventors: Michael P. Fleming, Longmont, CO (US); Yeun-Kwei Han, Louisville, CO (US); Lewis M. Hodges, Longmont, CO (US); David A. Johnston, Louisville, CO (US); Roger P. Micheli, Louisville, CO (US); Kurt Puentener, Basel (CH); Chris R. Roberts, Berthoud, CO (US); Michelangelo Scalone, Birsfelden (CH); Mark A. Schwindt, Boulder, CO (US); Robert J. Topping, Longmont, CO (US)

(73) Assignee: Roche Colorado Corporation, Boulder, CO (US)

(*) Notice: Subject to any disclaimer, the term of this patent is extended or adjusted under 35 U.S.C. 154(b) by 0 days.

(21) Appl. No.: 09/668,834

(22) Filed: Sep. 22, 2000

Related U.S. Application Data

(60) Provisional application No. 60/180,560, filed on Feb. 4, 2000.

(51) Int. Cl.[7] ............................................. C07D 309/32

(52) U.S. Cl. ..................................... 549/292; 549/294

(58) Field of Search .............................. 549/292, 294

(56) References Cited

U.S. PATENT DOCUMENTS

| | | | |
|---|---|---|---|
| 4,962,242 A | 10/1990 | Yamada et al. | 568/822 |
| 5,066,815 A | 11/1991 | Sayo et al. | 549/319 |
| 5,144,057 A | 9/1992 | Eyer | 560/51 |
| 5,194,671 A | 3/1993 | Meier | 560/126 |
| 5,245,056 A | 9/1993 | Karpf et al. | 549/510 |
| 5,274,143 A | 12/1993 | Ramig et al. | 554/123 |
| 5,399,720 A | 3/1995 | Karpf et al. | 549/292 |
| 5,420,305 A | 5/1995 | Ramig et al. | 549/292 |
| 5,945,559 A | 8/1999 | Sotoguchi et al. | 560/174 |

OTHER PUBLICATIONS

Landl, John J. et al., "A New Route to β–Keto–δ–lactones: Practical Preparation of (R)–3–Hexyl–5, 6–dihydro–4–hydroxy–6–undecyl–2H–pyran–2–one, a Key Intermediate in Asymmetric Synthesis of Tetrahydrolipstatin," Tetrahedron Letters, vol. 34, No. 2, pp. 277–280 (1993).
Miura, Katsukiyo et al., "Triethylborane Induced Perfluoroalkylation of Silyl Enol Ethers and Ketene Silyl Acetals with Perfluoroalkyl Iodides," Bull. Chem. Soc. Jpn., vol. 64, No. 5, pp. 1542–1553 (1991).
Umemoto, Teruo et al., "1H,1H–Perfluoroalkylation of Enol Silyl Ethers with (1H,1H–Perfluoroalkyl)–phenyliodonium Triflates. A New Method for the Preparation of β– and δ–Trifluoromethyl Carbonyl Compounds and Their Higher Perfluoroalkyl Homologues)," Bull. Chem. Soc. Jpn., vol. 60, pp. 3823–3825 (1987).
Sugimoto, Jiro et al., "Triethylborane Induced Radical Reaction of Ketene Silyl Acetals with Polyhalomethanes. Synthesis of 3,3–Dihalo– and 3–Haloacrylates," The Chemical Society of Japan, Chemistry Letters, pp. 1319–1322 (1991).
Miura, Katsukiyo et al., "Triethylborane Induced Radical Reaction of Keten Silyl Acetals with Polyhalomethanes," Bull. Chem. Soc. Jpn. vol. 65, pp. 1513–1521 (1992).
Shono, Tatsuya et al., "Electroorganic Chemistry. 82. β–Amino Acid Esters from α–Methoxycarbamates and Ketene Silyl Acetals; Cyclization to β–Lactams," J. Org. Chem. vol. 49, pp. 1056–1059 (1984).
Purrington, Suzanne T. et al., "Preparation of α–Fluoro Carboxylic Acids and Derivatives," J. Org. Chem., vol. 55, pp. 3423–3424 (1990).
Clay, Ronald J. et al., "A Safe, Economical Method for the Preparation of β–Oxo Esters," Synthesis, pp. 290–292 (1993).
Rathke, Michael W. et al., "Procedures for the Acylation of Diethyl Malonate and Ethyl Acetoacetate with Acid Chlorides Using Tertiary Amine Bases and Magnesium Chloride," J. Org. Chem, vol. 50, pp. 2622–2624 (1985).
Pommier, Agnes et al., "An Asymmetric Synthesis of (—)-Tetrahydrolipstatin," Synthesis, pp. 1294–1295 (1994).
Schmid, R. et al., "Asymmetric hydrogenation in process research of pharmaceuticals, vitamins and fine chemicals," Chiral Europe (1994).
Case–Green, Stephen C. et al., "Asymmetric Synthesis of (—)-Tetrahydrolipstatin," Synlett, pp. 781–782, Nov. 1991.
Kitamura, Masato et al., "Asymmetric Synthesis of β–Hydroxy Sulfonic Acids by BINAP/Ru–Catalyzed Hydrogenation," Tetrahedron, vol. 55, pp. 8769–8785 (1999).
Pye, Philip J. et al., "[2.2]PHANEPHOS–Ruthenium(II) Complexes: Highly Active Asymmetric Catalysts for the Hydrogenation of β–Ketoesters," Tetrahedron Letters, vol. 39, pp. 4441–4444 (1998).

*Primary Examiner*—Ba K. Trinh
(74) *Attorney, Agent, or Firm*—Townsend and Townsend and Crew LLP

(57) ABSTRACT

The present invention relates to a novel process for producing a δ-lactone of the formula:

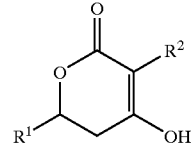

using an acyl halide of the formula:

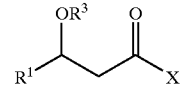

wherein $R^1$, $R^2$ $R^3$ and X are described herein, as well as novel intermediates. In particular, the present invention relates to a process for enantioselectively producing the (R)-δ-lactone.

35 Claims, No Drawings

SYNTHESIS OF 3,6-DIALKYL-5,6-DIHYDRO-4-HYDROXY-PYRAN-2-ONE

CROSS-REFERENCES TO RELATED APPLICATIONS

This application claims the benefit of U.S. Provisional Application No. 60/180,560, filed Feb. 4, 2000, which is incorporated herein by reference in its entirety.

FIELD OF THE INVENTION

The present invention is directed to a process for producing 3,6-dialkyl-5,6-dihydro-4-hydroxy-pyran-2-one. In particular, the present invention is directed to an enantioselective process for producing the same.

BACKGROUND OF THE INVENTION

δ-Lactones, including pyranones such as 3,6-dialkyl-5,6-dihydro-4-hydroxy-pyran-2-ones are useful intermediates in the preparation of a variety of fine chemicals and pharmaceutically active compounds. For example, 3-hexyl-4-hydroxy-6-undecyl-5,6-dihydro-pyran-2-one is a well known precursor for the preparation of oxetanones such as tetrahydrolipstatin. See for example, U.S. Pat. Nos. 5,245,056 and 5,399,720, both issued to Karpf et al.; and U.S. Pat. Nos. 5,274,143 and 5,420,305, both issued to Ramig et al.

One method of preparing 3,6-dialkyl-5,6-dihydro-4-hydroxy-pyran-2-ones such as 3-hexyl-4-hydroxy-6-undecyl-5,6-dihydro-pyran-2-one involves intramolecular cyclization of α-haloesters, typically (α-bromoesters, using a metal as a reducing agent. Broadly, this type of reaction is generally known as an intramolecular Reformatsky reaction. For example, the above mentioned U.S. Pat. Nos. 5,274,143 and 5,420,305, both issued to Ramig et al. disclose intramolecular Reformatsky using a "low valent metal" such as zinc, Li, Na, K and the like including amalgams of Zn such as Zn(Cu) and Zn(Ag).

While a variety of metals may be used in the Reformatsky reaction, it is generally believed and widely accepted that some metals such as magnesium cannot be generally used in the Reformatsky reaction. See for example, *Advanced Organic Chemistry*, 3$^{rd}$ ed., March, J., John Wiley & Sons, New York, N.Y., 1985, pp. 822–824. However, the use of magnesium is more desirable than zinc in industrial processes, because the magnesium waste can be more easily disposed of and is less hazardous to the environment than the zinc waste. Moreover, many Reformatsky reactions, including those disclosed in U.S. Pat. Nos. 5,274,143 and 5,420,305, use ether as a solvent (see Examples 5, 10 and 12), which has a low boiling point, i.e., less than 40° C., which may result in a high concentration of solvent vapor within the production facility, thereby creating a potentially hazardous condition, especially in large scale production facilities.

Other methods of preparing tetrahydrolipstatin use a β-hydroxy ester, e.g., methyl 3-hydroxy tetradecanoate, as an intermediate. See for example, Pommier et al., *Synthesis*, 1994, 1294–1300, Case-Green et al., *Synlett.*, 1991, 781–782, Schmid et al., *Proceedings of the Chiral Europe'94 Symposium*, Sep. 19–20, 1994, Nice, France, and the above mentioned U.S. Patents. Some methods of preparing oxetanones, such as those disclosed in the above mentioned U.S. Patents issued to Karpf et al., use a β-hydroxy ester as an intermediate to prepare the δ-lactone which is then used in the synthesis of oxetanones.

The stereochemistry of a molecule is important in many of the properties of the molecule. For example, it is well known that physiological properties of drugs having one or more chiral centers, i.e., stereochemical centers, may depend on the stereochemistry of a drug's chiral center. Thus, it is advantageous to be able to control the stereochemistry of a chemical reaction.

Many oxetanones, e.g., tetrahydrolipstatin, contain one or more chiral centers. Intermediates such as δ-lactones and β-hydroxy esters in the synthesis of tetrahydrolipstatin contain one chiral center. Some syntheses of these intermediates, such as those disclosed in the above mentioned U.S. Patents issued to Karpf et al., are directed to preparation of a racemic mixture which is then resolved at a later stage to isolate the desired isomer. Other methods are directed to an asymmetric synthesis of the β-hydroxy ester by enantioselectively reducing the corresponding β-ketoester.

Moreover, in order to achieve a high yield of the desired product, some current asymmetric hydrogenation processes for reducing methyl 3-oxo-tetradecanoate require extremely pure reactants, e.g., hydrogen gas purity of at least 99.99%, thus further increasing the cost of producing the corresponding β-hydroxy ester.

Therefore, there is a need for a process for producing δ-lactones which does not require zinc based Reformatsky-type reactions. There is also a need for enantioselective reduction of β-ketoesters under conditions which do not require extremely pure reactants or high hydrogen gas pressure.

SUMMARY OF THE INVENTION

One embodiment of the present invention provides a process for the preparation of a δ-lactone of the formula:

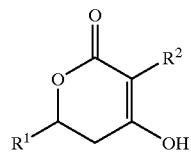

comprising contacting an α-halo ester of the formula:

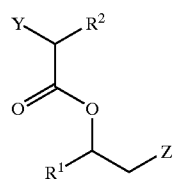

with a reactive species generating reagent selected from the group consisting of Grignard reagents, magnesium, magnesium-sodium mixtures, samarium, manganese, and mixtures thereof under conditions sufficient to produce said δ-lactone, where $R^1$ is $C_1$–$C_{20}$ alkyl; $R^2$ is H or $C_1$–$C_{10}$ alkyl; Y is a halide; and Z is nitrile, ester, amide, hydroxyamino amide, acid halide, anhydride, carboxyl carbonate or carboxyl haloformate.

Another embodiment of the present invention provides a process for producing (6R)-3-hexyl-4-hydroxy-6-undecyl-5, 6-dihydropyran-2-one comprising contacting an α-bromo ester of the formula:

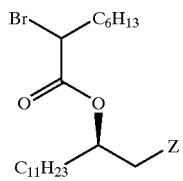

with a reactive species generating reagent described above under conditions sufficient to produce (6R)-3-hexyl-4-hydroxy-6-undecyl-5,6-dihydropyran-2-one, where Z is nitrile or a moiety of the formula —C(=O)W; W is $C_1$–$C_6$ alkoxide, $C_6$–$C_{20}$ aryloxide, $C_7$–$C_{20}$ arylalkoxide, halide, $C_1$–$C_6$ carboxylate or a moiety of the formula —NR$^3$R$^4$; and each of R$^3$ and R$^4$ is independently $C_1$–$C_6$ alkyl, $C_6$–$C_{20}$ aryl, $C_7$–$C_{20}$ arylalkyl, $C_1$–$C_6$ alkoxide, $C_6$–$C_{20}$ $C_7$–$C_{20}$ arylalkoxide or R$^3$ and R$^4$ together form a moiety of the formula —(CR$^5$R$^6$)$_a$—Q—(CR$^7$R$^8$)$_b$—; each of R$^5$, R$^6$, R$^7$ and R$^8$ is independently H or $C_1$–$C_6$ alkyl, $C_6$–$C_{20}$ aryl, $C_7$–$C_{20}$ arylalkyl; Q is O, NR$^9$ or S; R$^9$ is H, an amine protecting group, $C_1$–$C_6$ alkyl, $C_6$–$C_{20}$ aryl or $C_7$–$C_{20}$ arylalkyl; and each of a and b is independently an integer from 1 to 4.

Yet another embodiment of the present invention provides a compound of the formula:

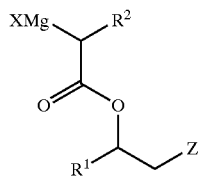

or its corresponding enolate of the formula:

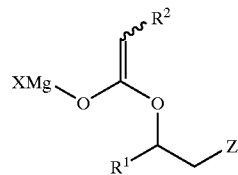

where R$^1$ is $C_1$–$C_{20}$ alkyl; R$^2$ is H or $C_1$–$C_{10}$ alkyl; X is a halide; and Z is nitrile, ester, amide, hydroxyamino amide, acid halide, anhydride, carboxyl carbonate or carboxyl haloformate. A particularly preferred compound of the present invention is of the formula:

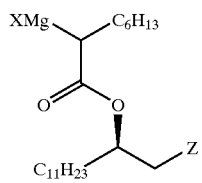

or its corresponding enolate of the formula:

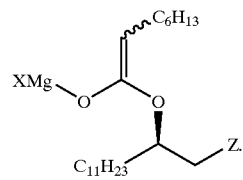

Preferably, Z is an ester. More preferably Z is a moiety of the formula —C(=O)OMe or —C(=Ot-Bu.

Still yet another embodiment of the present invention provides a process for producing β-ketoester of the formula:

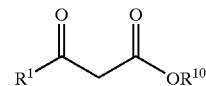

comprising:
(a) contacting an alkyl acetoacetate of the formula CH$_3$C(=O)CH$_2$C(=O)OR$^{10}$, with a magnesium alkoxide, preferably magnesium methoxide, under conditions sufficient to produce a magnesium salt of said alkyl acetoacetate and a first alcohol, preferably methanol, and removing at least a portion of said first alcohol;
(b) contacting said alkyl acetoacetate magnesium salt with an alkyl acyl halide of the formula R$^1$C(=O)X, preferably lauroyl chloride, under conditions sufficient to produce a tricarbonyl compound of the formula R$^1$C(=O)CH[C(=O)CH$_3$]C(=O)OR$^{10}$; and
(c) contacting said tricarbonyl compound with a second alcohol, preferably methanol, under conditions sufficient to produce said β-ketoester, wherein
X is a halide, preferably chloride;
R$^1$ is $C_1$–$C_{20}$ alkyl, preferably undecyl; and
R$^{10}$ is $C_1$–$C_6$ alkyl, $C_6$–$C_{20}$ aryl or $C_7$–$C_{20}$ arylalkyl, preferably methyl.

Preferably, the reaction is carried out in a non-polar organic solvent, more preferably a solvent that forms an azeotrope with the alcohol that is generated in the reaction mixture, and most preferably toluene.

The reaction temperature of the step (a) is at least about 40° C., preferably at least about 45° C.

The reaction temperature of the step (b) is at least about 50° C., preferably at least about 60° C.

The reaction temperature of the step (c) is at least about 70° C., preferably at least about 75° C.

Preferably, the step (c) is carried without adding any acid or base.

DETAILED DESCRIPTION

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "alkyl" refers to aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, pentyl, hexyl, heptyl, octyl, decyl and undecyl.

The term "aryl" refers to monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl. Exemplary aryl groups include phenyl, toluyl, pyrrolyl, thiophenyl, furanyl, imidazolyl, pyrazolyl, 1,2,4-triazolyl, pyridinyl, pyrazinyl, pyrimidinyl, pyridazinyl, thiazolyl, isothiazolyl, oxazolyl, and isoxazolyl.

The present invention provides a process for the preparation of δ-lactones, including pyranones, such as 3,6-dialkyl-5,6-dihydro-4-hydroxy-pyran-2-ones. In particular, the present invention provides a process for the preparation of a δ-lactone of the formula:

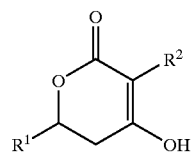

I where $R^1$ is $C_1$–$C_{20}$ alkyl, preferably undecyl; and $R^2$ is H or $C_1$–$C_{10}$ alkyl, preferably hexyl. The present invention also provides a process for enantioselectively producing the δ-lactone I. In one embodiment of the present invention, the enantioselective process provides (6R)-δ-lactone I, i.e., a compound of the formula:

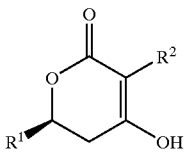

IA

It should be appreciated that the δ-lactone of formula I and the corresponding enantiomerically enriched δ-lactone IA may also exist in, or are in equilibrium with, their tautomeric forms:

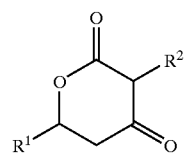

II and

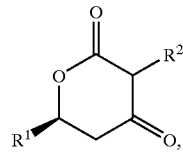

IIA respectively. Therefore, any reference to the δ-lactone of formula I or IA implicitly includes its tautomeric form of formula II or IIA, respectively.

The present invention will now be described in reference to the syntheses of enantiomerically enriched δ-lactone IA. It should be appreciated that the racemic form of δ-lactone I or δ-lactones having the opposite stereochemical configuration as that of formula IA, while not explicitly discussed herein, can be readily prepared using the processes of the present invention by using a racemic mixture or opposite stereochemically configured starting materials, respectively.

One embodiment of the present invention provides a process for preparing the δ-lactone IA by treating an (R)-(α-halo ester of the formula:

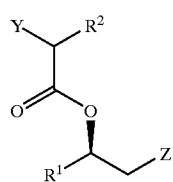

III with a reactive species generating reagent selected from the group consisting of Grignard reagents, magnesium, magnesium-sodium mixtures, samarium, manganese, and mixtures thereof under conditions sufficient to produce the δ-lactone IA, where $R^1$ and $R^2$ are as described above; Y is a halide, preferably bromide; and Z is nitrile (—CN) or a moiety of the formula —C(=O)W; where W is $C_1$–$C_6$ alkoxide, $C_6$–$C_{20}$ aryloxide, $C_7$–$C_{20}$ arylalkoxide, halide, $C_1$–$C_6$ carboxylate (i.e., —OC(=O)R', where R' is H or $C_1$–$C_5$ alkyl), haloformate (i.e., —OC(=O)$Y^1$, where $Y^1$ is a halide) or a moiety of the formula —$NR^3R^4$, where each of $R^3$ and $R^4$ is independently $C_1$–$C_6$ alkyl, $C_6$–$C_{20}$ aryl, $C_7$–$C_{20}$ arylalkyl, $C_1$–$C_6$ alkoxide, $C_6$–$C_{20}$ aryloxide, $C_7$–$C_{20}$ arylalkoxide or $R^3$ and $R^4$ together form a cyclic moiety of the formula —$(CR^5R^6)_a$—Q—$(CR^7R^8)_b$—, where each of $R^5$, $R^6$, $R^7$ and $R^8$ is independently H or $C_1$–$C_6$ alkyl, $C_6$–$C_{20}$ aryl, $C_7$–$C_{20}$ arylalkyl; Q is O, $NR^9$ or S; $R^9$ is H, an amine protecting group, $C_1$–$C_6$ alkyl, $C_6$–$C_{20}$ aryl or $C_7$–$C_{20}$ arylalkyl; and each of a and b is independently an integer from 1 to 4. A variety of amine protecting groups are known in the art, and can be employed. Examples of many of the possible amine protecting groups can be found in *Protective Groups in Organic Synthesis*, 3rd edition, T. W. Greene and P. G. M. Wuts, John Wiley & Sons, New York, 1999, which is incorporated herein by reference in its entirety.

As used herein, the term "reactive species generating reagent" refers to a reagent or a compound which generates a reactive intermediate species from an α-halo ester compound III which can undergo an intramolecular cyclization reaction to produce the δ-lactone I. Preferably, the reactive species generating reagent is a Grignard reagent or magnesium metal. More preferably, the reactive species generating reagent is a Grignard reagent.

Preferably, Z is selected from the group consisting of morpholino amide (i.e., —C(=O)W, where W is morpholine moiety), N,O-dimethylhydroxylamino amide (i.e., —C(=O)W, where W is —N(CH$_3$)(OCH$_3$), nitrile (i.e., —CN), acid chloride (i.e., —C(=O)Cl), pivaloyl anhydride (i.e., —C(=O)W, where W is —OC(=O)t-Bu), methyl ester, ethyl ester and t-butyl ester.

It is widely held and accepted that in general Grignard species cannot be formed from α-halo esters. See *Advanced Organic Chemistry*, 3$^{rd}$ ed., March, J., John Wiley & Sons, New York, N.Y., 1985, 822–824. But see, *Org. Synthesis*, 1973, 53, 1882; Kelly, *Tet. Lett.*, 1985, 26, 2173–2176; and MMJ, *J Amer. Chem. Soc.*, 1990, 112, 7659–7672. However, surprisingly and unexpectedly, the present inventors have found that treating an (α-halo ester III with magnesium produces the δ-lactone IA. Without being bound by any theory, it is believed that adding magnesium metal to α-halo ester III results in initial formation of an intermediate, α-magnesium halide ester species, which undergoes the intramolecular cyclization reaction. Furthermore, it is believed that addition of a Grignard reagent to α-halo ester III results in a metal-halide exchange reaction again forming an α-magnesium halide ester species, which undergoes an intramolecular cyclization reaction to produce the δ-lactone IA.

Typically, the reaction is carried out in an aprotic organic solvent such as tetrahydrofuran (THF), n-butyl ether, dimethoxy ethane (DME), methyl t-butyl ether (MTBE), toluene, 2-methyltetrahydrofuran or the like, preferably under an inert atmosphere such as nitrogen, argon, helium or the like.

An intramolecular cyclization reaction which forms the δ-lactone IA can be favored over intermolecular reaction by having a relatively low concentration of the α-halo ester III. Preferably, the concentration of α-halo ester III is about 2.5 M or less, more preferably about 2.0 M or less, and most preferably about 1.5 M or less.

The reaction temperature is generally from about 40° C. to about 65° C. However, the reaction temperature depends on a variety of factors such as the solvent used and the presence or absence of one or more additives in the reaction mixture, which is discussed in detail below.

One particular aspect of the present invention provides a process for producing δ-lactone IA by treating the α-halo ester III with a Grignard reagent. Without being bound by any theory, it is believed that addition of a Grignard reagent to the α-halo ester III results in a metal-halide exchange to produce a reactive species, e.g., α-magnesium halide ester, which undergoes an intramolecular cyclization reaction to produce the cyclized product δ-lactone IA. When a Grignard reagent is used as a reactive species generating agent in equal to or less than stoichiometric amount relative to the α-halo ester III, it is believed that the initially formed cyclized intermediate, which collapses to form the magnesium organometallic species of Compound I and methanol (where Z is —COOMe), reacts with the basic α-magnesium halide ester or the added Grignard reagent which may be present in the reaction mixture, thereby resulting in a relatively low yield of the δ-lactone IA.

The yield of the δ-lactone IA can be increased significantly by adding an excess amount of the Grignard reagent. In this manner, the excess Grignard reagent is used to quench, i.e., deprotonate, compounds deriving from the collapse of the initially formed cyclized intermediate or any other compounds which contain an acidic proton. Thus, preferably the amount of Grignard reagent added is from about 2 to about 10 equivalents, more preferably from about 2 to about 5 equivalents, still more preferably from about 3 to about 5 equivalents, and most preferably about 3 equivalents.

Any Grignard reagent can be used in the present invention including a variety of substituted and unsubstituted aryl and alkyl Grignard reagents including methyl, ethyl, isopropyl, butyl, sec-butyl, tert-butyl, 2-methoxyphenyl, t-amyl, t-octyl, hexyl, pentyl, and 1-octyl magnesium halides, such as magnesium bromides and magnesium chlorides. Preferred Grignard reagents include tert-butyl magnesium chloride and tert-butyl magnesium bromide. A more preferred Grignard reagent is tert-butyl magnesium chloride.

While the α-halo ester III and the reactive species generating reagent can be combined or added in any sequence, it has been found that when the reactive species generating reagent is a Grignard reagent a simultaneous addition of the α-halo ester III and the Grignard reagent is particularly preferred. For example, simultaneous addition of 13.6 mL solution of 30.7 mmol of methyl (3R)-3-[(2-bromo-1-oxooctyl)oxy]-tetradecanoate in tetrahydro-furan (THF) and 3 equivalents of tert-butyl magnesium chloride in 86 mL of THF over a one hour period to a 60° C. reaction vessel containing about 10 mL of THF solvent resulted in 97% yield (A.N., i.e., area normalized) of (6R)-3-hexyl-4-hydroxy-6-undecyl-5,6-dihydropyran-2-one when the crude product was analyzed by a gas chromatography 1 hr after the complete addition of reagents.

Processes of the present invention can also include the step of adding an additive selected from the group consisting of trapping agents, metal activators, Lewis acid rate enhancers, and mixtures thereof.

As used herein, the term "trapping agent" refer to a compound which can prevent internal proton quench of the reactive species generating reagent, e.g., a Grignard reagent, or the in situ generated reactive intermediate species, e.g., α-magnesium halide ester. Exemplary trapping agents include amines such as triethylamine, diisopropylethylamine, tributyl-amine, and 2,2,6,6-tetramethylpiperidine, which form amine hydrohalides;, anhydrides and acyl chlorides, which can react with the initially formed intramolecular cyclization product to form enol esters; halocarbonates, including chloroformates such as methyl chloroformate and benzyl chloroformate, which can react with the initially formed intramolecular cyclization product to form enol carbonates; and silylating agents such as silyl chlorides, including trimethylsilyl chloride, tert-butydimethylsilyl chloride, and triisopropylsilyl chloride, and hexamethyldisilazane, which can react with the initially formed intramolecular cyclization product to form silyl enol ethers. When a trapping agent such as an anhydride, an acyl chloride, a halocarbonate, or a silylating agent is present, the resulting intermediate product (e.g., an enol ester, an enol carbonate, or a silyl enol ether, respectively) may be isolated and/or purified before producing the desired δ-lactone I. The isolated and/or purified intermediate product can be readily converted into the desired δ-lactone I by deprotection of the enol ester, the enol carbonate, or the silyl enol ether. Such deprotection reactions are well known to one of ordinary skill in the art.

The term "metal activator" refers to a compound which activates a metal (i.e., magnesium, magnesium-sodium mixtures, samarium, manganese, or mixtures thereof) in the formation of a reactive intermediate species. Exemplary metal activators include 1,2-dibromoethane; 1-bromo-2-chloroethane; anthracene; iodine; other metals, such as sodium; metal salts, such as zinc chloride, magnesium chloride, magnesium bromide, magnesium iodide, and iron salts including iron bromides, iron cyclopentadienes; and mixtures thereof. Preferably, the metal activator is selected from the group consisting of 1,2-dibromoethane, iodine, sodium, zinc chloride, iron bromides (e.g., ferric bromide), magnesium chloride, magnesium bromide, magnesium iodide, and mixtures thereof. The metal can be pretreated with the metal activator prior to addition of the α-halo ester III, for example, iodine can be added to the metal and the mixture may be heated prior to addition of the (α-halo ester III. Alternatively, the metal activator can be added simultaneously or after addition of the α-halo ester III to the reaction mixture containing the metal. For example, 1,2-dibromoethane can be added to a mixture of the metal and the α-halo ester III. Typically, the amount of metal activator added is from about 100 parts per million (ppm) to about 100,000 ppm relative to the α-halo ester III. The use of a metal activator is particularly preferred when the reactive species generating reagent is magnesium metal.

The term "rate enhancer" includes "Lewis acid rate enhancer" and refers to a compound which increases the rate of intramolecular cyclization reaction of the reactive intermediate species, e.g., α-magnesium halide ester. Exemplary Lewis acid rate enhancers which are useful in the present invention include magnesium metal; magnesium salts, such as magnesium bromide, magnesium chloride, magnesium iodide, magnesium acetate, and other organic and inorganic magnesium salt; alkyl aluminum compounds, such as trialkyl aluminum compounds (e.g., triethyl aluminum, tributyl aluminum, trimethyl aluminum); alkyl halide aluminum compounds, such as diethyl aluminum chloride, methyl aluminum dichloride; aluminum halides such as aluminum trichloride; and non-Lewis acid rate enhancers such as Reike magnesium, aluminum metal, cyclopentadiene, and anthracene. Preferably, the rate enhancer and is selected from the group consisting of zinc halides, iron halides, magnesium halides, trialkyl aluminum compounds, cyclopentadiene, anthracene, and mixtures thereof.

When Z in α-halo ester III is an ester moiety (i.e., a moiety of the formula —C(=O)OR"), an alkoxide scavenger may be added to the reaction mixture to prevent the alkoxide which is formed in the reaction from interfering with the formation of the δ-lactone IA. Unless the context requires otherwise, the term "alkoxide" refers to an alkoxide generated from the ester moiety of the Z group, i.e., —OR" group of the moiety of the formula —C(=O)OR". As used herein an "alkoxide scavenger" refers to a compound which reacts with the alkoxide or the corresponding protonated hydroxy compound to form a relatively non-reactive compound or a moiety which physically traps the alkoxide or the corresponding protonated hydroxy compound, thereby preventing the alkoxide or the corresponding protonated hydroxy compound from interfering with the desired reaction. Exemplary alkoxide scavengers include silyl halides, such as trimethylsilyl chloride, t-butyldimethylsilyl chloride and other silyl halides which form silyl ethers with the alkoxide; metals such as aluminum, magnesium and other metals which form a relatively inert metal alkoxides; molecular sieves, which entrap the alkoxide within their physical structures; and other alkoxide deactivating compounds, such as activated basic alumina, deprotonated silica gel (e.g., from a reaction between silica gel and n-butyl lithium).

Processes of the present invention can also include the step of producing the α-halo ester III which comprises contacting a (R)-β-hydroxy compound of the formula:

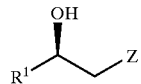

IV with an α-halo activated carbonyl compound of the formula:

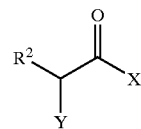

V in the presence of a base under conditions sufficient to produce the α-halo ester III, where $R^1$, $R^2$, Y and Z are as described above, and X is a halide, preferably chloride or bromide (or Compound V may comprise a mixtures of chloride and bromide compounds), or $C_1$–$C_{10}$ carboxylate (i.e., —OC(=O)R, where R is H or $C_1$–$C_9$).

Reaction between β-hydroxy compound IV and the α-halo activated carbonyl compound V is typically conducted in an aprotic organic solvent such as hexane, ether, and those described above, preferably under an inert atmosphere. Exemplary bases which are useful in producing α-halo ester III from β-hydroxy compound IV and α-halo activated carbonyl compound V include tertiary amines, such at triethylamine, tributylamine and dimethylaminopyridine (DMAP); pyridine; carbonates such as potassium carbonate, sodium carbonate, lithium carbonate, cesium carbonate, and aqueous solutions of such bases; bicarbonates such as sodium bicarbonate, potassium bicarbonate, lithium bicarbonate, and aqueous solutions of such bases; other relatively non-nucleophilic and mildly basic, i.e., having pKa of about 16 or less, and preferably pKa of about 10 or less, compounds. Other examples of reaction conditions for producing α-halo ester III from β-hydroxy compound IV and α-halo activated carbonyl compound V are disclosed in the above mentioned U.S. Pat. Nos. 5,420,305 and 5,274,143, which are incorporated herein by reference in their entirety. The α-halo ester III thus produced can be used directly without any further purification, or it can be purified, e.g., by distillation under reduced pressure, prior to its use.

The α-halo activated carbonyl compound V can be readily prepared, for example, by halogenating the corresponding activated carbonyl compound (i.e., where Y is H) with α-halogenating agent such as bromine. In one specific example, bromine is added to octanoyl chloride at temperature of about 55° C., which resulted in formation of a mixture of α-bromooctanoyl chloride and α-bromooctanoyl bromide. This mixture can be used without further purification, as both of these compounds undergo a similar esterification reaction with the β-hydroxy compound IV to produce the same corresponding α-halo ester III.

The activated carbonyl compound in turn can be readily prepared from the corresponding carboxylic acid or esters by using a method known to one of ordinary skill in the art, including the use of anhydrides, or acyl halogenating agents. Exemplary acyl halogenating agents and general procedures for using the same are disclosed, for example, in "Comprehensive Organic Synthesis," vol. 6, Trost, Fleming and Winerfeldt eds., Pergamon Press, 1991, pp. 301–319, and "The Chemistry of Acyl Halides," Patai, ed., Interscience Publishers, 1972, pp. 35–64, which are incorporated herein by reference in their entirety.

Processes of the present invention can also include the step of enantioselectively producing the β-hydroxy compound IV by an enantioselective reduction of a β-keto compound of the formula:

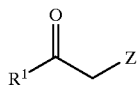

VI where $R^1$ and Z are as described above.

In one particular embodiment of the present invention, where Z is a moiety of the formula —C(=O)W, especially where W is $C_1$–$C_6$ alkoxide, $C_6$–$C_{20}$ aryloxide or $C_7$–$C_{20}$ arylalkoxide, the β-hydroxy compound IV is produced from a β-ketoester of the formula:

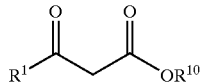

VII by hydrogenating the ketone carbonyl of the β-ketoester VII in the presence of a chiral hydrogenation catalyst, where $R^1$ is as described above and $R^{10}$ is $C_1$–$C_6$ alkyl, $C_6$–$C_{20}$ aryl or $C_7$–$C_{20}$ arylalkyl. Preferably $R^{10}$ is $C_1$–$C_6$ alkyl, more preferably methyl, or ethyl. The —$OR^{10}$ moiety can be interchanged with other groups by a variety of methods known to one of ordinary skill in the art including by transesterification, amide formation, acyl halide formation, saponification and other methods which are disclosed in a variety of references including *Advanced Organic Chemistry*, 3rd ed., March, J., John Wiley & Sons, New York, N.Y., 1985, which is incorporated herein by reference in its entirety.

It should be appreciated that a non-chiral hydrogenation catalyst will result in racemic mixture of β-hydroxy compound IV, and a chiral hydrogenation catalyst having an opposite configuration as those described below will result in β-hydroxy compound having an opposite configuration as that shown in FIG. IV. One embodiment of the present invention provides a process for enantioselectively reducing the β-ketoester VII using an enantiomerically enriched hydrogenation catalyst, i.e., hydrogenation catalyst having greater than about 97% enantiomeric excess (% ee).

In one particular embodiment of the present invention, the chiral hydrogenation catalyst comprises a ruthenium catalyst containing a chiral ligand such as those shown in the Examples section, including a catalyst of the formula:

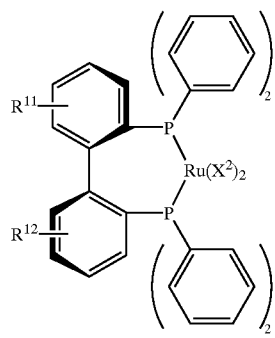

where each $X^2$ is independently a halide, such as iodide, bromide or preferably chloride; or acetate; and each of $R^{11}$ and $R^{12}$ is independently H, $C_1$–$C_6$ alkyl or $C_1$–$C_6$ alkoxy, provided at least one of $R^{11}$ or $R^{12}$ is not H. Moreover, each phenyl group may contain more than one $R^{11}$ or $R^{12}$ groups. Furthermore, one or both of the phenyl groups of the biphenyl moiety may be replaced with other aromatic groups such as a naphthyl, pyridyl or other substituted aryl groups.

One of the useful hydrogenation catalyst of the present invention is a product produced by contacting a ruthenium diacetate of the formula Ru(OAc)$_2$((R)-MeOBIPHEP) with a halide source, such as alkaline metal halides (e.g., LiX, NaX, KX and CsX, where X is a halide) or hydrohalides (e.g., HX, where X is a halide), preferably hydrochloric acid, where Ru(OAc)$_2$((R)-MeOBIPHEP) is a compound of the formula:

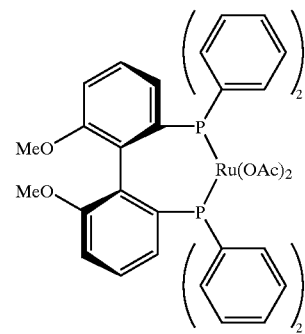

Without being bound by any theory, it is believed that treating Ru(OAc)$_2$((R)—MeOBIPHEP) with hydrochloric acid results in replacing both of the OAc groups with chloride; thus, the resulting product is believed to be Ru(Cl)$_2$((R)-MeOBIPHEP). Interestingly, however, when Ru(OAc)$_2$((R)-MeOBIPHEP) is treated with less than about 2 equiv. of HCl, the resulting hydrogenation catalyst does not produce (R)-3-hydroxy compound IV in a high enantiomeric excess. Surprisingly and unexpectedly, in some cases such a chiral hydrogenation catalyst produces predominantly (S)-3-hydroxy compound. However, when at least about 5 equiv. of HCl is added to Ru(OAc)$_2$((R)-MeOBIPHEP), preferably at least about 10 equiv. and more preferably at least about 20 equiv., the resulting chiral hydrogenation catalyst enantioselectively reduces the β-ketoester VII to the corresponding (3R)-3-hydroxy compound IV.

The precursor of chiral hydrogenation catalyst of the present invention, i.e., ruthenium dicarboxylate diphosphine compound or [Ru(OC(=O)R')$_2$(diphosphine)], can be prepared according the following reaction scheme:

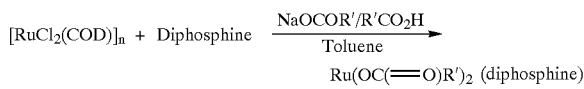

$$[RuCl_2(COD)]_n + \text{Diphosphine} \xrightarrow[\text{Toluene}]{\text{NaOCOR'/R'CO}_2\text{H}} Ru(OC(=O)R')_2 \text{ (diphosphine)}$$

In this manner a variety of chiral ruthenium dicarboxylate diphosphine, including those listed in Example 16, can be prepared. The process for preparing a ruthenium dicarboxylate diphosphine compound generally involves contacting [RuCl$_2$(COD)]$_n$, which is commercially available or preferably prepared according to the procedure of Albers et al., *Inorg. Synth.*, 1989, 26, 68, with a mixture of a carboxylate salt and the corresponding carboxylic acid, i.e., MOC(=O)R' and HOC(=O)R' mixture, such as sodium acetate/acetic acid and sodium pivalate/pivalic acid mixtures, in an aprotic organic solvent, preferably toluene. The mixture is heated at a temperature of about 80° C. to about 120° C., preferably about 100° C. A typical reaction time is from about 15 hours to about 72 hours, preferably from about 20 hours to about 48 hours. The amount of carboxylate salt used can be about 2 equiv. to about 50 equiv., preferably about 2 equiv. to about 25 equiv., more preferably about 2.1 equiv. to about 10 equiv., and most preferably about 2.5 equiv. Preferably a small excess of [RuCl$_2$(COD)]$_n$ is used relative to the diphosphine compound to ensure complete conversion of the diphosphine compound.

While commercially available [RuCl$_2$(COD)]$_n$ complex can be used, it has been found that freshly prepared [RuCl$_2$(COD)]$_n$ complex from ruthenium trichloride generally affords shorter reaction time, more consistent and/or higher yield of ruthenium dicarboxylate diphosphine compound. In this manner, a one-pot synthesis of ruthenium dicarboxylate diphosphine compound can be achieved from inexpensive and readily available ruthenium trichloride.

The β-hydroxy compound (e.g., (3R)-3-hydroxy compound) IV can be further purified, i.e., enantiomerically enriched, by recrystallizing the initial product to afford a product having at least about 99% ee. Therefore, it should be appreciated that depending on the cost of a particular chiral hydrogenation catalyst, it may be more economical to use a chiral hydrogenation catalyst which provides less than about 95% ee of the β-hydroxy compound IV, which can be further enantiomerically enriched by recrystallization.

Unlike currently used ruthenium-based hydrogenation catalysts for asymmetric reduction of methyl 3-oxotetradecano-late, the hydrogenation catalyst of the present invention does not require high purity conditions, e.g., hydrogen gas having purity of at least about 99.99%, to produce methyl 3-hydroxytetradecanoate in high yield and high enantiomeric excess. In fact, the asymmetric hydrogenation of methyl 3-oxotetradecanoate under technical grade conditions, e.g., hydrogen gas having purity of about 99.5% and nitrogen gas having purity of about 99.5%, using the hydrogenation catalyst of the present invention proceeds with a substantially similar rate as those requiring high purity reaction conditions. Moreover, the hydrogenation catalyst of the present invention allows the use of lower hydrogen gas pressure, thereby reducing the cost of initial capital investments and reducing the potential danger associated with high pressure hydrogen gas reaction conditions. In addition, by using asymmetric hydrogenation processes described above, the present invention allows asymmetric synthesis of the δ-lactone I without a need for resolving any racemic intermediates.

Typically, hydrogenation of β-ketoester VII, e.g., methyl 3-oxotetradecanoate, is conducted in a conventional hydrogenation solvent including an alkyl alcohol, such as ethanol or preferably in methanol, at a reaction temperature of about 80° C. The concentration of the substrate (i.e., β-ketoester VII) in hydrogenation reaction is generally at about 40 wt %, and the ratio of HCl to Ru(OAc)$_2$((R)-MeOBIPHEP) in the hydrogenation catalyst is about 20:1. A typical ratio of methyl 3-oxotetradecanoate to the hydrogenation catalyst is from about 5000:1 to about 50,000:1. To this reaction mixture, typically from about 40 bars to about 80 bars of technical grade hydrogen gas is added, and the reaction is allowed to proceed for about 4 hours (h).

In this manner, the β-hydroxy compound IV, such as methyl (R)-3-hydroxy tetradecanoate, can be produced in at least about 90% isolated yield from the corresponding β-ketoester VII, more preferably in at least about 93% isolated yield and most preferably in at least about 95% isolated yield. The enantiomeric excess of β-hydroxy compound IV produced is at least about 90% ee, preferably at least about 95% ee, and more preferably at least about 99% ee. The enantiomeric excess can be increased to at least about 95% ee after a single recrystallization, preferably at least about 99% ee, and most preferably at least about 99.5% ee.

The β-ketoester VII can be readily prepared by a variety of known methods. See for example, Viscontini et al., *Helv. Chim. Acta*, 1952, 284, 2280–2282, Case-Green, *Synlett*, 1991, 781–782, and U.S. Pat. No. 5,945,559, issued to Sotoguchi et al., which are incorporated herein by reference in their entirety. However, the present inventors have found that the β-ketoester VII, in particular where R$^1$ is undecyl, can be readily obtained in high yield, preferably at least about 85% yield, by the following process. Addition of alkyl acetoacetate, e.g., methyl acetoacetate, to a non-polar solution of magnesium alkoxide, e.g., magnesium methoxide in toluene, and heating the mixture to at least about 100° C. with removal of any alkyl alcohol that is generated, e.g., from protonation of magnesium alkoxide, produces magnesium salt of alkyl acetoacetate. Addition of an acyl chloride compound, e.g., lauroyl chloride, to the resulting alkyl acetoacetate magnesium salt at about 60° C. produces a tri-carbonyl compound. Heating the tri-carbonyl compound, preferably to at least about 70° C., in the presence of an alcohol, preferably methanol, provides the β-ketoester VII in at least about 80% yield, preferably at least about 85% yield.

Additional objects, advantages, and novel features of this invention will become apparent to those skilled in the art upon examination of the following additional examples thereof, which are not intended to be limiting.

EXAMPLES

Example 1

This example illustrates a method for producing 2-bromooctanoyl halide.

To a 1-L, 3-necked round bottomed flask fitted with a mechanical stirrer, Claisen adapter with thermocouple-J-KEM controller, nitrogen inlet and addition funnel was added 271.5 g (1.67 mol) of octanoyl chloride under a blanket of nitrogen. The addition funnel was filled with 374 g (2.34 mol) of bromine. The octanoyl chloride was heated to 55° C. and the bromine was added slowly over about 8 hours (h). The reaction mixture was stirred overnight at 55° C. The reaction mixture was distilled under reduced pressure. The product began distilling over with a pot temperature at 113° C. and a vapor temperature of 111° C. at 8 mm Hg of pressure. In order to maintain a steady flow of distillate the pot temperature was increased to 127° C. and vapor temperature to 119° C. at 8 mm Hg of pressure. The resulting 451 g of clear liquid (100% yield) was a mixture of 2-bromooctanoyl chloride and 2-bromooctanoyl bromide (ratio 35:65) by GC analysis.

Example 2

This example illustrates a method for producing methyl (3R)-3-[(2-bromo-1-oxooctyl)oxy]tetradecanoate.

To a 500-mL, 3-necked round bottomed flask fitted with a mechanical stirrer, Claisen adapter with $N_2$ inlet, thermocouple-J-KEM controller and a rubber septum/addition funnel was added 50 g (193 mmol) of solid methyl (3R)-3-hydroxytetradecanoate. The solid was dissolved in 400 mL of hexane and the solution cooled to 0° C. A mixture of 2-bromooctanoyl chloride/bromide (62.5 g, 1.2 equiv.) from Example 1 was added. The addition funnel was filled with 19.1 g (24 mmol) of pyridine and 100 mL of hexane. The pyridine solution was added slowly over 30 minutes. The addition funnel was then rinsed with 25 mL of hexane. The resulting thick yellowish-white slurry was stirred for about two hours at about 0° C., then 200 mL of water and 200 mL of hexane were added. The quenched reaction mixture was allowed to settle and the water layer separated. The product was extracted into the top organic layer. The top organic layer was washed one time with 100 mL of water. The combined bottom aqueous layers were washed two times with 100 mL of hexane. The organic layers were combined, dried ($MgSO_4$), filtered, and the solvent removed on the rotary evaporator. The resulting product was a clear oil weighing 96.0 g (107% yield).

Example 3

This example illustrates a method for producing (6R)-3-hexyl-4-hydroxy-6-undecyl-5,6-dihydropyran-2-one.

To a 1-L, 3-necked, round-bottomed flask fitted with a Claisen adapter with $N_2$ inlet, a West condenser and a thermocouple-J-KEM controller and a rubber septum was added 13.9 g (0.572 g-atom, 3.2 equiv.) of magnesium (from Chromasco) was added. A small flake of 12 (about 45 mg) was added and the mixture was heated to about 80° C. 1,2-Dibromoethane (3.4 g, 18 mmol) and 350 mL of THF were added to the hot $Mg/I_2$ mixture to activate the metal surface. Methyl (3R)-3-[(2-bromo-1-oxooctyl)oxy]-tetradecanoate (82.9 g, 179 mmol) from Example 2, 1,2-dibromoethane (33.6 g, 179 mmol) and 400 mL of THF were added to the addition funnel. This mixture was slowly added to the Mg/THF mixture at reflux over about 1 h. The reaction mixture was stirred overnight (14 h) at about 60° C. The resulting yellow solution was decanted away from the metal into a 1-L, round-bottomed flask. The residual Mg metal was rinsed twice with 60 mL of THF. The combined THF solution was concentrated on a rotary evaporator. The syrupy mixture was taken up in 1750 mL of methylene chloride and added to a mixture of 500 mL of water, 200 mL of ice and 98 mL of 10% HCl in a separatory funnel. The aqueous layer was removed, the organic layer washed once with 200 mL of saturated sodium chloride, dried ($NaSO_4$), filtered, and the solvent removed on a rotary evaporator. The crude white solid (66.7 g) was slurried in 100 mL of hexane, cooled to 0° C., filtered, and rinsed twice with 50 mL of cold hexane. The isolated white solid was dried in an oven at 40° C. under reduced pressure (10 mm Hg) overnight resulting in 28.4 g of (6R)-3-hexyl-4-hydroxy-6-undecyl-5,6-dihydropyran-2-one (45–50% yield based on methyl (R)-3-hydroxytetradecanoate).

Example 4

This example illustrates a method for producing (6R)-3-hexyl-4-hydroxy-6-undecyl-5,6-dihydropyran-2-one using tri-methylsilyl chloride (TMSCl).

To magnesium turnings (3.65 g, 3 equiv.) in THF (100 mL) was added $I_2$ (0.11 g, 1%). The resulting mixture was heated to reflux 2 h, which resulted in a pale yellow solution. To this solution at 50° C. was added a mixture of methyl (3R)-3-[(2-bromo-1-oxooctyl)oxy]-tetradecanoate from Example 2 (22.9 g, 1 equiv.) and dibromoethane (9.4 g, 1 equiv.) over 50 min. Five minutes after starting the addition of the substrates, TMSCl (12 mL, 2 equiv.) was added over 1 min. At the same time i-PrMgCl (25.5 mL of a 2 M solution, 0.9 equiv.) was added over a period of 50 minutes. The addition of the Grignard reagent was completed 5 minutes after completion of the substrate.

The reaction mixture was stirred for a total of 3.5 h (calculated from the first addition of substrates) at 50° C.

The reaction mixture was concentrated and the resulting residue was diluted with 200 mL of EtOAc and quenched with 100 mL of 10% HCl. The mixture was stirred for 30 minutes. The organic phase was separated, and washed successively with 50 mL of 10% HCl and 50 mL of $H_2O$. The resulting mixture was concentrated, diluted with 100 mL of hexanes, stirred at 0° C. for 5 minutes, filtered, and the crystals were washed with hexanes (2×50 mL, 0° C).

Drying of the crystals afforded 6.8 g (39%) of (6R)-3-hexyl-4-hydroxy-6-undecyl-5,6-dihydropyran-2-one.

Example 5

This example illustrates a method for producing (6R)-3-hexyl-4-hydroxy-6-undecyl-5,6-dihydropyran-2-one using molecular sieves (3 A) as a methanol (or methoxide) scavenger.

To magnesium turnings (3.65 g, 3 equiv.) in THF (100 mL) was added 12 (0.11 g, 1%). The resulting mixture was heated to reflux for 1.5 h which turned to a pale yellow solution. To this solution was added 8.5 g of activated pulverized 3 A molecular sieves. The mixture was heated to reflux for 30 min., then dibromoethane and methyl (3R)-3-[(2-bromo-1-oxooctyl)oxy]-tetradecanoate from Example 2 were added over 45 minutes at reflux.

The mixture was heated to reflux for 4 h after starting addition of the substrates.

Workup as described in Example 4 gave 6.8 g (39%) of (6R)-3-hexyl-4-hydroxy-6-undecyl-5 ,6-dihydropyran-2-one.

Example 6

This example also illustrates the effect of different phosphine ligands on the ruthenium hydrogenation catalyst on the yield and % ee of asymmetric hydrogenation of β-ketoester.

The hydrogenation reaction of β-ketoester 1 of Example 7 was conducted using $Ru(OAc)_2$(Phosphine) with 20 equivalents of HCl at 60° C., under $H_2$ (70 bar) in methanol, with concentration of β-ketoester 1 at 30% wt. The identity of phosphine ligand, % isolated yield and (% ee) are shown below:

| Phosphine | Acronym | % yield[1] | % ee[2] |
|---|---|---|---|
| (structure) | BIPHEMP | 45 | 99 |
| (structure) | MeOBIPHEP | 28 | 99 |
| (structure) | TriMeOBIPHEP | 27 | 98 |
| (structure) | TMBTP | 65 | 99 |
| (structure) | BITIANP | nd | nd |

-continued

| Phosphine | Acronym | % yield[1] | % ee[2] |
|---|---|---|---|
| | BIBFUP | 17 | 97 |
| | BIPHOMP | nd | nd |
| | mTol-BIPHEMP | 61 | 97 |
| | pTol-MeOBIPHEP | 27 | 99 |
| | 3,5-tBu-MeOBIPHEP | 66 | 99 |

-continued

| Phosphine | Acronym | % yield[1] | % ee[2] |
|---|---|---|---|
| | 3,5-tPe-MeOBIPHEP | 98 | 94 |
| | 3,5-MOR-MeOBIPHEP | 13 | 75 |
| | 3,5-TMS-MeOBIPHEP | nd | nd |

-continued

| Phosphine | Acronym | % yield[1] | % ee[2] |
|---|---|---|---|
| | 3,5-CF$_3$-MeOBIPHEP | nd | nd |
| | 3,5-tBu-4-MeO-MeOBIPHEP | 50 | 96 |
| | 3,5-Xyl-4-MeO-MeOBIPHEP | 46 | 96 |
| | 3,5-iPr-4DMA-MeOBIPHEP | nd | nd |

-continued

| Phosphine | Acronym | % yield[1] | % ee[2] |
|---|---|---|---|
| (structure) | 3,4,5-MeO-MeOBIPHEP | nd | nd |
| (structure) | Cy-MeOBIPHEP | 1 | nd |
| (structure) | 6-MeO-2-Naphthyl-MeOBIPHEP | 19 | 96 |
| (structure) | PHANEPHOS | nd | nd |
| (structure) | BPPM | nd | nd |

| Phosphine | Acronym | % yield[1] | % ee[2] |
|---|---|---|---|
| 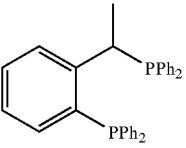 | MEBEP | 25 | 58 |

[1]% yield after 1 h
[2]% ee after 16 h
nd = not determined

Example 7

This example illustrates the effect of additives on the yield and % ee of asymmetric hydrogenation of β-ketoester.

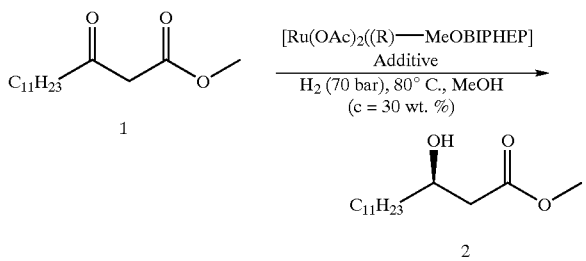

TABLE 1

Asymmetric Hydrogenation: Influence of Additive*

| en-try[1] | Additive | conversion | | | | | 2 % ee |
|---|---|---|---|---|---|---|---|
| | | 1 h | 2 h | 4 h | 6 h | 16 h | |
| 1 | 2 eq. HCl | 4 | 8 | 13 | 19 | 50 | 36(S) |
| 2 | 20 eq. HCl | 98 | >99.9 | | | | 99 |
| 3 | 30 eq. LiCl | 87 | 99.7 | 99.9 | >99.9 | | 97 |
| 4 | 20 eq. HBr | 31 | 59 | 78 | 82 | 91 | 46 |
| 5 | 20 eq. HBF$_4$ | 3 | 6 | 17 | 27 | 77 | 33(S) |
| 6 | 20 eq. p-TsOH | 50 | 79 | 96 | 98 | 99.8 | 62 |
| 7 | 2 eq. HCl + 4% wt.[2] CH$_2$Cl$_2$ | 32 | 66 | 90 | 97 | >99.9 | 71 |
| 8 | 2 eq. HCl + 18 eq. HBF$_4$ | 12 | 29 | 47 | 63 | 90 | 17(S) |
| 9 | 20 eq. Bu$_4$NI | <1 | <1 | <1 | <1 | <1 | — |

*Ratio of β-ketoester 1 to the catalyst = about 50,000:1.
[1]All gases >99.99990% purity.
[2]Relative to β-ketoester 1.

Example 8

This example illustrates the effect of different phosphine ligands on the ruthenium hydrogenation catalyst on the yield and % ee of asymmetric hydrogenation of β-ketoester.

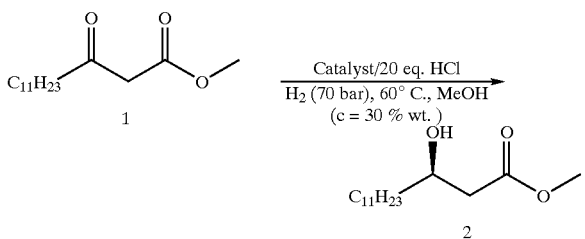

TABLE 2

Asymmetric Hydrogenation: Influence of Phosphines*

| en-try[1] | Additive | conversion | | | | | 2 % ee |
|---|---|---|---|---|---|---|---|
| | | 1 h | 2 h | 4 h | 6 h | 16 h | |
| 1* | [Ru(OAc)$_2$((R)-MeOBIPHEP)] | 26 | 48 | 94 | >99.9 | | 99 |
| 2* | [Ru(OAc)$_2$((R)-3,5-tBu-MeOBIPHEP)] | 66 | 99.5 | >99.9 | | | 99 |
| 3* | [Ru(OAc)$_2$((R)-BIPHEMP)] | 45 | 91 | >99.9 | | | 99 |
| 4* | [Ru(OAc)$_2$((S)-BINAP)] | 31 | 57 | 99.7 | >99.9 | | 96(S) |
| 5** | [Ru(OAc)$_2$((R,R)-NORPHOS)] | 7 | 14 | 27 | 39 | 90 | 64 |
| 6** | [Ru(OAc)$_2$((R,R)-CHIRAPHOS)$_2$] | <1 | <1 | <1 | <1 | 1 | — |
| 7** | [RuCl(p-cym)((R,R)-Me-DUPHOS)]Cl[2] | <1 | <1 | <1 | <1 | 1 | — |
| 8** | [RuCl(p-cym)((R)-MeOBIPHEP)]Cl[2] | 45 | 99 | >99.9 | | | 99 |

*Ratio of β-ketoester 1 to the catalyst = about 50,000:1.
**Ratio of β-ketoester 1 to the catalyst = about 5,000:1.
[1]All gases >99.99990% purity.
[2]No HCl used.

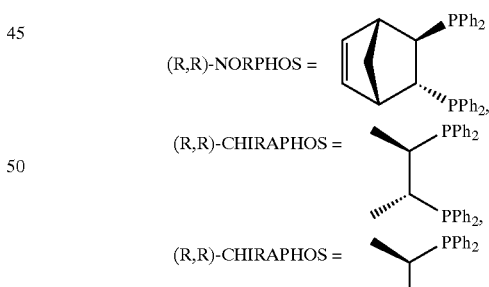

and p-cym=p-cymene.

Example 9

This example illustrates a method for producing (6R)-3-hexyl-5,6-dihydro-4-hydroxy-6-undecyl-pyran-2-one using tert-butylmagnesium chloride.

In a 500 mL 3-necked round bottom flask fitted with a Claisen head with N$_2$ inlet, a West condenser, a thermocouple-J-KEM controller and an addition funnel was added a solution of tert-butylmagnesium chloride (341 mL of a 1.0 M solution, 341 mmole, 3 equiv.) at about 60° C. Methyl-(R)-3-(2'-bromo-1'-oxooctyloxy)tetradecanoate (52.6.0 g, 113.5 mmole, 1 equiv.) ("bromodiester") and 25 mL of dry THF were added to an addition funnel. The bromodiester mixture was slowly added to the t-BuMgCl/ THF mixture at reflux over about one hour. The reaction mixture was sampled at 1 and 2 hours at about 60° C. (resulting in 90 and 91% area normalized gas chromatography (AN GC) analysis, respectively). After 2 hours the resulting reaction mixture was cooled and concentrated on a roto-evaporator to about ⅓ to about ½ the original volume. The resulting syrupy mixture was taken up in about 250 mL of toluene (or an ether, such as methyl tert-butyl ether and the like; a hydrocarbon, such as hexane, heptane, and the like; or mixtures thereof) and added to a mixture containing 250 mL of toluene, 75 mL of 10% HCl in a 1 L jacketed flask keeping the quenched solution below 30° C. The aqueous layer was removed. The organic layer washed one time with 50 mL of 1.0 N HCl solution. The aqueous layer was removed, the organic layer washed one time with 50 mL of water, dried over magnesium sulfate, filtered and concentrated. This resulted in a gel-like solid residue. The residue was dissolved in 250 mL of ethyl acetate at 40° C. The ethyl acetate was removed on the roto-evaporator. The resulting crude off-white solid (42.4 g) was slurried up in about 100 mL of hexane and cooled to 0° C., filtered and rinsed with 50 mL of cold hexane followed by another 25 mL of cold hexane. The isolated white solids were air dried under vacuum for about 1 to 2 hours resulting in 31.4 g of (6R)-3-hexyl-5,6-dihydro-4-hydroxy-6-undecyl-pyran-2-one (78.4% yield).

Example 10

This example illustrates a method for producing (6R)-3-hexyl-5,6-dihydro-4-hydroxy-6-undecyl-pyran-2-one using tert-amylmagnesium chloride.

In a 500 mL 3-necked round bottom flask fitted with a Claisen head with $N_2$ inlet, a West condenser, a thermocouple-J-KEM controller and an addition funnel, a solution of tert-amylmagnesium chloride (341 mL of a 1.0 M solution in $Et_2O$, 341 mmole, 3 equiv.) was added. The $Et_2O$ was replaced with THF and heated to about 60° C. Methyl-(R)-3-(2'-bromo-1'-oxooctyloxy)-tetradecanoate (52.6.0 g, 113.5 mmole, 1 equiv.) and 25 mL of dry THF was added to an addition funnel. The starting bromodiester mixture was slowly added to the t-amylMgCl/THF mixture at reflux over about one hour.

The reaction mixture was sampled at 1 and 2 hours at about 60° C. (resulting in 81 and 80% AN GC analysis, respectively). After about 2 hours the resulting reaction mixture was cooled and concentrated to about ⅓ to about ½ the original volume. The resulting syrupy mixture was diluted with about 250 mL of toluene and added to a stirred mixture containing about 250 mL of toluene and about 75 mL of 10% HCl in a 1 L jacketed flask while maintaining the quenched solution below about 30° C. The aqueous layer was removed. The organic layer was washed successively with about 50 mL of 1.0 N HCl solution and 50 mL of water, dried over magnesium sulfate, filtered and concentrated to yield a solid residue.

The residue was dissolved in about 400 mL of ethyl acetate at about 40° C. The ethyl acetate was removed on the roto-evaporator. The resulting crude off-white solid (42.3 g) was slurried up in about 100 mL of hexane and cooled to about 0° C., filtered and rinsed with about 50 mL of cold hexane followed by another about 35 mL of cold hexane. The isolated white solids were air dried under vacuum for about 1 to 2 hours resulting in 27.6 g of (6R)-3-hexyl-5,6-dihydro-4-hydroxy-6-undecyl-pyran-2-one (69.1% yield).

Example 11

This example illustrates a process for producing a β-ketoester 1 of Example 7.

Into a 250 mL three necked round bottomed flask equipped with a mechanical stirrer and reflux condenser under nitrogen was added 1.54 g of magnesium powder (99.5% pure, 50 mesh) and methanol (about 50 mL). The resulting mixture was heated to reflux overnight. The reflux condenser was replaced with a distillation head. Toluene (about 150 mL) was added and methanol was removed by azeotropic distillation until a head temperature of 104° C. was reached. Approximately 82 mL of distillate was collected.

To the resulting reaction mixture was added 29 g of methyl acetoacetate at 45 ° C. Methanol generated from the reaction was removed by distillation until a head temperature of about 104° C. was reached. Approximately 62 mL of distillate was collected. The reaction mixture was cooled to room temperature. The resulting mixture was then heated to about 60° C. and lauroyl chloride (20.71 g) in 20 mL of toluene was added over 2 hours, maintaining the reaction mixture at about 60° C. The resulting mixture was stirred for another 60 minutes. GC analysis showed that less than 1% lauroyl chloride remained.

Methanol (14.4 mL) was added and the resulting mixture was heated to about 70° C. and stirred for 4 hours. Another 9.0 mL of methanol was added and the resulting mixture was heated to 75° C. for an additional 20 hours. The resulting mixture was cooled to room temperature and the reaction was quenched by the addition of concentrated HCl (19.43 g) maintaining the temperature of the mixture below 35° C. The lower aqueous phase was separated, and the toluene phase was washed with water (2×45 mL), aqueous potassium bicarbonate (0.75 g in 36 mL of water), and then washed with water (36 mL). Toluene was removed under a rotoevaporator (75° C. at about 25–30 mmHg) to afford the product in 86.6 % yield (21.03 g, 92% A.N. by GC).

Example 12

This example illustrates a synthetic process for producing [Ru(OAc)$_2$((S)-BINAP)].

Under an argon atmosphere, a 25-mL 2-necked round-bottomed flask equipped with a reflux condenser was charged with (S)-BINAP (0.50 g. 0.80 mmol), 0.25 g (0.84 mmol) of [RuCl$_2$(COD)]$_n$, sodium acetate (0.33 g, 4.0 mmol) and toluene/acetic acid 1:1 (5 mL). The brown reaction mixture was stirred in an oil bath at 100° C. for 25 h. Thereafter, the volatiles were removed by rotatory evaporation, the residue was diluted with dichloromethane (5 mL) and the resulting yellow-brown suspension was filtered through celite. The filter cake was washed with dichloromethane (9 mL) in three portions, and the combined filtrates were concentrated and dried under high vacuum overnight at room temperature (r.t.). The brown oil was diluted in ether/hexane 1:1 (4 mL) and stirred for 30 min at r.t. to give a solid precipitate. The supernatant was removed by suction with a micro-filter candle and the residue was washed with hexane (5 mL) at r.t. and dried overnight. The crude product was diluted in methanol (5 mL) and stirred for 1 h at 50° C., 1 h at r.t. (formation of a precipitate), and finally 1 h at 0° C. The supernatant was removed as above, the residue was washed with methanol (2 mL) at 0° C. and dried overnight under high vacuum at r.t. to give [Ru(OAc)$_2$((S)-BINAP)] (0.48 g, 72% relative to S-BINAP) as a brown crystalline powder. $^{31}$P NMR: δ 65.2 ppm (s).

Example 13

This example illustrates a synthetic process for producing [Ru(OAc)$_2$((R)-BIPHEMP)].

Under an argon atmosphere a 50-mL 2-necked round-bottomed flask equipped with a reflux condenser was charged with (R)-BIPHEMP (2.01 g, 3.65 mmol), [RuCl2(COD)]$_n$ (1.13 g, 3.83 mmol), sodium acetate (1.5 g, 18.2 mmol) and toluene/acetic acid 1:1 (20 mL). The brown reaction mixture was stirred in an oil bath at 100° C. for 31 h. The volatiles were removed by rotatory evaporation, and the residue was diluted with dichloromethane (20 mL) and the, resulting yellow-brown suspension was filtered through celite. The filter cake was washed with dichloromethane (12 mL) in three portions and the combined filtrates were concentrated, diluted with methanol (10 mL) and stirred for 1 h at 50° C., 1 h at r.t. (formation of a precipitate), and finally 1 h at 0° C. The supernatant was removed by suction with a micro-filter candle, the residue was washed with methanol (6 mL) at 0° C. and dried overnight under high vacuum at r.t. to give [Ru(OAc)$_2$((R)-BIPHEMP)] (2.48 g, 88% relative to (R)-BIPHEMP) as a brown crystalline powder. $^{31}$P NMR: δ 65.4 ppm (s).

Example 14

This example illustrates a synthetic process for producing [Ru(OAc)$_2$((R)-3,5-t-Bu-MeOBIPHEP)].

Under an argon atmosphere a 25-mL 2-necked round-bottomed flask equipped with a reflux condenser was charged with (R)-3,5-tBu-MeOBIPHEP (0.50 g, 0.49 mmol), [RuCl$_2$(COD)]$_n$ (0.14 g, 0.51 mmol), sodium acetate (0.20 g, 2.44 mmol) and toluene/acetic acid 1:1 (5 mL). The brown reaction mixture was stirred in an oil bath at 100° C. for 26 h, and the volatiles were removed under high vacuum. The resulting residue was diluted with hexane (10 mL) and the resulting yellow-brown suspension was filtered through celite. The filter cake was washed with hexane (9 mL) in three portions and the combined filtrates were concentrated and dried overnight under high vacuum at r.t. yielding [Ru(OAc)$_2$((R)-3,5-t-Bu-MeOBIPHEP)] (0.62 g, 99% relative to (R)-3,5-t-Bu-MeOBIPHEP) as a brown crystalline powder.

Example 15

This example illustrates a synthetic process for producing [Ru((CH$_3$)$_3$CCO$_2$)$_2$((R)—MeOBIPHEP)].

Under an argon atmosphere a 25-mL 2-necked round-bottomed flask equipped with a reflux condenser was charged with (R)-MeOBIPHEP (1.06 g, 1.82 mmol), [RuCl$_2$(COD)]$_n$ (0.56 g. 2.00 mmol) and toluene (2 mL). To this mixture a solution obtained by dissolving sodium hydride (0.22 g, 9.1 mmol) in a mixture of toluene (3 mL) and pivalic acid (6.0 g, 59 mmol) was added and the resulting brown reaction mixture was stirred in an oil bath at 100° C. for 72 h, cooled, diluted with pentane (15 mL), and filtered through celite. The filter cake was washed successively with pentane (15 mL) in three portions and dichloromethane (25 ml) in four portions, the combined CH$_2$Cl$_2$ filtrates were concentrated and the resulting residue was dried overnight under high vacuum at r.t. The crude product was treated with methanol (10 mL) under stirring for 1 h at 50° C., 1 h at r.t., and finally 30 min at 0° C. The supernatant was removed by suction with a micro-filter candle, the residue was washed with methanol (5 mL) at 0° C. and dried overnight under high vacuum at r.t. to give [Ru((CH$_3$)$_3$CCO$_2$)$_2$((R)-MeOBIPHEP)] (0.66 g, 41% relative to (R)-MeOBIPHEP) as a brown crystalline give powder. $^{31}$P NMR: δ 64.9 ppm (s).

Example 16

This example illustrates a synthetic process for producing [Ru(OAc)$_2$(COD)].

Under an argon atmosphere a 50-mL 2-necked round-bottomed flask equipped with a reflux condenser was charged with [RuCl$_2$(COD)]$_n$ (1.01 g, 3.59 mmol), sodium acetate (1.47 g, 18.0 mmol and toluene/acetic acid 1:1 (20 ml). The brown reaction mixture was stirred in an oil bath at 100° C. for 4 h, the volatiles were removed by rotatory evaporation, and the residue was dried overnight under high vacuum at r.t. The resulting dark brown residue was diluted with toluene (10 mL) and filtered through celite. The filter cake was washed with toluene (15 mL) in three portions and the combined filtrates were concentrated. The resulting residue was diluted with dichloromethane (20 mL) and washed with water (8 mL) in two portions. The combined organic layers were dried over magnesium sulfate, filtered and the filter cake was washed with dichloromethane (15 mL) in three portions. The combined, yellow-brown filtrates were concentrated, and the resulting residue was diluted with pentane (5 mL), stirred for 30 min at 0° C., and the supernatant was removed by suction with a micro-filter candle. This process repeated and the resulting residue was dried overnight at r.t. to yield [Ru(OAc)$_2$(COD)] (0.57 g, 49%) as a light brown crystalline powder.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent compounds, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for the preparation of a δ-lactone of the formula:

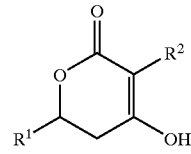

said process comprising contacting an α-halo ester of the formula:

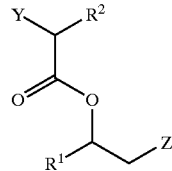

with a reactive species generating reagent comprising a Grignard reagent to produce said δ-lactone,
wherein
R$^1$ is C$_1$–C$_{20}$ alkyl;
R$^2$ is H or C$_1$–C$_{10}$ alkyl;
Y is a halide; and
Z is nitrile, ester, amide, hydroxylamino amide, acid halide, anhydride, carboxyl carbonate or carboxyl haloformate.

2. The process of claim 1, wherein $R^1$ is undecyl and $R^2$ is hexyl.

3. The process of claim 2, wherein Y is bromide.

4. The process of claim 3, wherein Z is selected from the group consisting of morpholino amide, N,O-dimethylhydroxylamino amide, nitrile, acid chloride, pivaloyl anhydride, methyl ester, ethyl ester and t-butyl ester.

5. The process of claim 4, wherein said reactive species generating reagent further comprises magnesium.

6. The process of claim 1, wherein said Grignard reagent is tert-butyl magnesium chloride or tert-butyl magnesium bromide.

7. The process of claim 1, wherein the ratio of said Grignard reagent to said α-halo ester is from about 2:1 to about 5:1.

8. The process of claim 1 further comprising the step of adding an additive selected from the group consisting of trapping agents, metal activators, rate enhancers, and mixtures thereof.

9. The process of claim 1 further comprising the step of producing said α-halo ester, wherein said α-halo ester producing step comprises contacting a β-hydroxy compound of the formula:

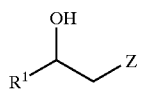

with an α-halo activated carbonyl compound of the formula:

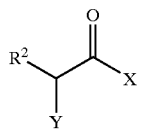

in the presence of a base under conditions sufficient to produce said α-halo ester, wherein X is a halide or $C_1$–$C_{10}$ carboxylate.

10. The process of claim 9, wherein said δ-lactone and said β-hydroxy compound have (R)stereoconfiguration.

11. The process of claim 10, further comprising the step of enantioselectively producing said β-hydroxy compound by enantioselective reduction of a β-keto compound of the formula:

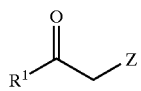

wherein said enantioselective reduction comprises hydrogenation of said β-keto compound in the presence of a chiral hydrogenation catalyst.

12. The process of claim 11, wherein said enantioselective reduction of said β-keto compound produces said β-hydroxy compound in an enantiomeric excess of at least about 90%.

13. The process of claim 11, wherein said chiral hydrogenation catalyst is a compound of the formula $RuCl_2((R)\text{-MeOBIPHEP})$.

14. The process of claim 11, wherein said chiral hydrogenation catalyst is the product produced by contacting a ruthenium diacetate of the formula $Ru(OAc)_2((R)\text{-MeOBIPHEP})$ with a halide source, wherein said halide source is selected from the group consisting of alkaline metal halides and hydrohalides.

15. The process of claim 14, wherein the molar ratio of said halide source to said ruthenium diacetate is at least about 20:1.

16. A process for producing (6R)-3-hexyl-4-hydroxy-6-undecyl-5,6-dihydropyran-2-one comprising contacting an α-halo ester of the formula:

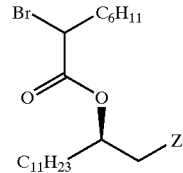

with a reactive species generating reagent comprising a Grignard reagent under conditions sufficient to produce said (6R)-3-hexyl-4-hydroxy-6-undecyl-5,6-dihydropyran-2-one, wherein
Z is nitrile or a moiety of the formula —C(=O)W;
W is $C_1$–$C_6$ alkoxide, $C_6$–$C_{20}$ aryloxide, $C_7$–$C_{20}$ arylalkoxide, halide, $C_1$–$C_6$ carboxylate or a moiety of the formula —$NR^3R^4$;
each of $R^3$ and $R^4$ is independently $C_1$–$C_6$ alkyl, $C_6$–$C_{20}$ aryl, $C_7$–$C_{20}$ arylalkyl, $C_1$–$C_6$ alkoxide, $C_6$–$C_{20}$ aryloxide, $C_7$–$C_{20}$ arylalkoxide or $R^3$ and $R^4$ together form a moiety of the formula —$(CR^5R^6)_a$—Q—$(CR^7R^8)_b$—;
each of $R^5$, $R^6$, $R^7$ and $R^8$ is independently H or $C_1$–$C_6$ alkyl, $C_6$–$C_{20}$ aryl, $C_7$–$C_{20}$ arylalkyl;
Q is O, $NR^9$ or S;
$R^9$ is H, an amine protecting group, $C_1$–$C_6$ alkyl, $C_6$–$C_{20}$ aryl or $C_7$–$C_{20}$ arylalkyl; and
each of a and b is independently an integer from 1 to 4.

17. The process of claim 16, wherein Z is selected from the group consisting of morpholino amide, N,O-dimethylhydroxylamino amide, nitrile, acid chloride, pivaloyl anhydride, methyl ester, ethyl ester and t-butyl ester.

18. The process of claim 16, wherein said reactive species generating reagent further comprises magnesium.

19. The process of claim 16, wherein said reactive species generating reagent is a Grignard reagent.

20. The process of claim 16, wherein the ratio of said Grignard reagent to said α-halo ester is from about 2:1 to about 5:1.

21. The process of claim 16 further comprising the step of adding an additive selected from the group consisting of trapping agents, metal activators, rate enhancers, and mixtures thereof.

22. The process of claim 16 further comprising the step of producing said α-halo ester, wherein said α-halo ester producing step comprises contacting a (R)-β-hydroxy compound of the formula:

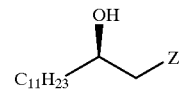

with an α-halo activated carbonyl compound of the formula:

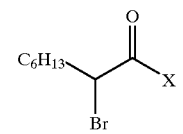

in the presence of a base under conditions sufficient to produce said α-halo ester, wherein X is Br or Cl.

23. The process of claim 22 further comprising the step of enantioselectively producing said (R)-β-hydroxy compound by enantioselective reduction of a β-keto compound of the formula:

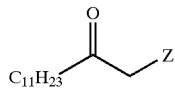

wherein said enantioselective reduction comprises hydrogenation of said β-keto compound in the presence of a chiral hydrogenation catalyst.

24. The process of claim 23, wherein said enantioselective reduction produces said β-hydroxy compound in an enantiomeric excess of at least about 90%.

25. The process of claim 23, wherein said chiral hydrogenation catalyst is a compound of the formula $RuCl_2((R)\text{-MeOBIPHEP})$.

26. The process of claim 23, wherein said chiral hydrogenation catalyst is the product produced by contacting a ruthenium diacetate of the formula $Ru(OAc)_2((R)\text{-MeOBIPHEP})$ with a halide source, wherein said halide source is selected from the group consisting of alkaline metal halides and hydrohalides.

27. The process of claim 26, wherein the molar ratio of said halide source to said ruthenium diacetate is at least about 20:1.

28. A process for producing (6R)-3-hexyl-4-hydroxy-6-undecyl-5,6-dihydropyran-2-one comprising:

(a) enantioselectively reducing a β-keto compound of the formula:

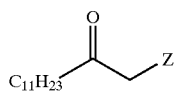

to produce a (R)-β-hydroxy compound of the formula:

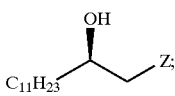

(b) contacting said (R)-β-hydroxy compound with an α-halo activated carbonyl compound of the formula:

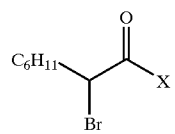

in the presence of a base under conditions sufficient to produce an α-halo ester of the formula:

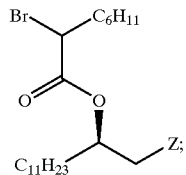

(c) contacting said α-halo ester with a reactive species generating reagent selected from the group consisting of Grignard reagents, metal and mixtures thereof under conditions sufficient to produce said (6R)-3-hexyl-4-hydroxy-6-undecyl-5,6-dihydropyran-2-one, wherein Z is nitrile or a moiety of the formula —C(=O)W;

W is $C_1$–$C_6$ alkoxide, $C_6$–$C_{20}$ aryloxide, $C_7$–$C_{20}$ arylalkoxide, halide, $C_1$–$C_6$ carboxylate or a moiety of the formula —$NR^3R^4$;

each of $R^3$ and $R^4$ is independently $C_1$–$C_6$ alkyl, $C_6$–$C_{20}$ aryl, $C_7$–$C_{20}$ arylalkyl, $C_1$–$C_6$ alkoxide, $C_6$–$C_{20}$ aryloxide, $C_7$–$C_{20}$ arylalkoxide or $R^3$ and $R^4$ together form a moiety of the formula —$(CR^5R^6)_a$—Q—$(CR^7R^8)_b$—;

each of $R^5$, $R^6$, $R^7$ and $R^8$ is independently H or $C_1$–$C_6$ alkyl, $C_6$–$C_{20}$ aryl, $C_7$–$C_{20}$ arylalkyl;

Q is O, $NR^9$ or S;

X is Br or Cl;

$R^9$ is H, an amine protecting group, $C_1$–$C_6$ alkyl, $C_6$–$C_{20}$ aryl or $C_7$–$C_{20}$ arylalkyl; and each of a and b is independently an integer from 1 to 4.

29. The process of claim 28, wherein Z is selected from the group consisting of morpholino amide, N,O-dimethylhydroxylamino amide, nitrile, acid chloride, pivaloyl anhydride, methyl ester, ethyl ester and t-butyl ester.

30. The process of claim 28, wherein said reactive species generating reagent is a Grignard reagent.

31. The process of claim 30, wherein said Grignard reagent is tert-butyl magnesium chloride or tert-butyl magnesium bromide.

32. The process of claim 28, wherein said enantioselective reduction comprises hydrogenation of said β-keto compound in the presence of a chiral hydrogenation catalyst of the formula $RuCl_2((R)\text{-MeOBIPHEP})$.

33. The process of claim 32, wherein said enantioselective reduction produces said β-hydroxy compound in an enantiomeric excess of at least about 90%.

34. The process of claim 32, wherein said chiral hydrogenation catalyst is the product produced by contacting a ruthenium diacetate of the formula $Ru(OAc)_2((R)\text{-MeOBIPHEP})$ with a halide source selected from the group consisting of alkaline metal halides, hydrohalides, and mixtures thereof.

35. The process of claim 34, wherein the molar ratio of said halide source to said ruthenium diacetate is at least about 20:1.

* * * * *